US011459466B2

(12) United States Patent
Kinlen et al.

(10) Patent No.: US 11,459,466 B2
(45) Date of Patent: *Oct. 4, 2022

(54) COMPOSITIONS AND COATINGS WITH NON-CHROME CORROSION INHIBITOR PARTICLES

(71) Applicant: The Boeing Company, Chicago, IL (US)

(72) Inventors: Patrick J. Kinlen, St. Louis, MO (US); Karen A. Schultz, Seattle, WA (US); Kenneth A. Krienke, Seattle, WA (US); Lawrence M. Lawless, Chesterfield, MO (US); Waynie M. Schuette, Troy, IL (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,380

(22) Filed: Nov. 6, 2019

(65) Prior Publication Data
US 2020/0071539 A1    Mar. 5, 2020
US 2022/0267610 A9    Aug. 25, 2022

Related U.S. Application Data (62) Division of application No. 14/852,065, filed on Sep. 11, 2015, now Pat. No. 10,508,203.
(Continued)

(51) Int. Cl.
*C09D 5/08* (2006.01)
*C23F 11/16* (2006.01)
(Continued)

(52) U.S. Cl.
CPC .......... *C09D 5/08* (2013.01); *C07D 285/125* (2013.01); *C09D 5/028* (2013.01); *C09D 5/082* (2013.01);
(Continued)

(58) Field of Classification Search
CPC .................. C09D 5/08–12; C09D 7/66–69
See application file for complete search history.

(56) References Cited

U.S. PATENT DOCUMENTS 2,636,861 A    4/1953   Watson
2,862,886 A    12/1958  Davies et al.
(Continued)

FOREIGN PATENT DOCUMENTS

CN    1218100 A      6/1999
CN    101929155 A    12/2010
(Continued)

OTHER PUBLICATIONS

Mercado, R.M.L. et al. Investigation of Zinc Dimercaptothiadiazole as a Corrosion Inhibitor for Steel. ECS Transactions, 2013, 50, 345-354. (Year: 2013).*
(Continued)

*Primary Examiner* — Stephen E Rieth
(74) *Attorney, Agent, or Firm* — MH2 Technology Law Group LLP (57) ABSTRACT

Compositions are described for protecting a metal surface against corrosion. The composition includes a corrosion-inhibiting particle. The corrosion inhibiting particle may be usable in an epoxy resin-based coating or an olefin resin-based coating. The particle may include a core and a protectant. The core may include a water soluble corrosion inhibitor. The protectant may be disposed on at least a portion of a surface of the core and may be covalently or ionically bonded to a thiol group of the corrosion inhibitor. The protectant may be configured to reduce reaction between the core and the epoxy resin or the olefin resin. Methods of making the compositions are also disclosed.

20 Claims, 8 Drawing Sheets

Related U.S. Application Data (60) Provisional application No. 62/055,939, filed on Sep. 26, 2014.

(51) Int. Cl.
    *C09D 163/00* (2006.01)
    *C09D 5/02* (2006.01)
    *C07D 285/125* (2006.01)

(52) U.S. Cl.
    CPC .......... *C09D 5/086* (2013.01); *C09D 163/00* (2013.01); *C23F 11/165* (2013.01)

(56) References Cited

U.S. PATENT DOCUMENTS

| | | | |
|---|---|---|---|
| 3,505,244 | A | 4/1970 | Cessna |
| 6,139,610 | A | 10/2000 | Sinko |
| 9,970,122 | B2* | 5/2018 | Lawless ................. C09K 15/30 |
| 10,508,203 | B2* | 12/2019 | Kinlen ................... C08L 81/02 |
| 2003/0072962 | A1 | 4/2003 | Katsuzaki et al. |
| 2004/0035498 | A1 | 2/2004 | Kinlen |
| 2004/0143037 | A1 | 7/2004 | Chang et al. |
| 2005/0183793 | A1 | 8/2005 | Kim et al. |
| 2006/0089273 | A1 | 4/2006 | Rowland |
| 2008/0216705 | A1* | 9/2008 | Hayes ..................... C09D 5/086 106/14.44 |
| 2008/0272341 | A1 | 11/2008 | Kinlen |
| 2008/0317962 | A1 | 12/2008 | Hayes et al. |
| 2010/0151253 | A1 | 6/2010 | Roth et al. |
| 2011/0236700 | A1 | 9/2011 | Hayes et al. |
| 2012/0085261 | A1 | 4/2012 | Barbe et al. |
| 2013/0017612 | A1 | 1/2013 | Li et al. |
| 2013/0052352 | A1 | 2/2013 | Cano-Iranzo et al. |
| 2014/0187672 | A1 | 7/2014 | Zhao et al. |
| 2014/0272364 | A1 | 9/2014 | Fitz et al. |
| 2014/0272392 | A1 | 9/2014 | Fitz et al. |

FOREIGN PATENT DOCUMENTS

| | | | |
|---|---|---|---|
| CN | 102391815 | A | 3/2012 |
| DE | 950805 | C | 10/1956 |
| DE | 3210540 | C1 | 1/1983 |
| FR | 2328024 | A1 | 5/1977 |
| JP | 2001335955 | A | 12/2001 |
| JP | 2001335965 | A | 12/2001 |
| JP | 2002129352 | A | 5/2002 |
| JP | 2003183684 | A | 7/2003 |
| JP | 2004156081 | A | 6/2004 |
| JP | 2004263252 | A | 9/2004 |
| JP | 2005154811 | A | 6/2005 |
| JP | 2005154812 | A | 6/2005 |
| JP | 2006082365 | A | 3/2006 |
| JP | 2006082366 | A | 3/2006 |
| JP | 2006082369 | A | 3/2006 |
| JP | 2006342419 | A | 12/2006 |
| JP | 2007009232 | A | 1/2007 |
| JP | 2007204770 | A | 8/2007 |
| JP | 2008238014 | A | 10/2008 |
| JP | 2008240042 | A | 10/2008 |
| JP | 2009287078 | A | 12/2009 |
| JP | 2009287080 | A | 12/2009 |
| JP | 4419532 | B2 | 2/2010 |
| JP | 4419533 | B2 | 2/2010 |
| JP | 2010201353 | A | 9/2010 |
| JP | 2011052253 | A | 3/2011 |
| JP | 2012077369 | A | 4/2012 |
| SU | 293036 | A1 | 1/1971 |
| SU | 1237681 | A1 | 6/1986 |
| SU | 1745741 | A1 | 7/1992 |
| WO | 99/18044 | A1 | 4/1999 |
| WO | 01/123444 | A1 | 2/2001 |
| WO | 01/92602 | A1 | 12/2001 |
| WO | 0192602 | A1 | 12/2001 |
| WO | 02/092880 | A1 | 11/2002 |
| WO | 03/089529 | A1 | 10/2003 |
| WO | 03089529 | A1 | 10/2003 |
| WO | 03/102034 | A1 | 12/2003 |
| WO | 2005049314 | A1 | 6/2005 |
| WO | 2006/075774 | A1 | 7/2006 |
| WO | 2007/008199 | A1 | 1/2007 |
| WO | 2016/049118 | A1 | 3/2016 |

OTHER PUBLICATIONS

Dispersetech LLC. Fineness of Grind. https://www.dispersetech.com/content/7-fineness-of-grind-. As viewed on Mar. 4, 2021. (Year: 2021).*
Second Notification of Office Action (both in English and Chinese) dated Jan. 30, 2019 in corresponding Chinese Application No. 201580050187.9.
Office Action dated Aug. 12, 2020 in corresponding Canadian Application No. 2,956,322, 3 pages.
Extended European Search Report dated Jul. 21, 2020 in related corresponding European Application No. 20166773.0, 12 pages.
M. Handrea-Haller, International Search Report and Written Opinion dated Dec. 7, 2015, PCT Application No. PCT/US2015/051609, filed Sep. 23, 2015, pp. 1-15.
Office Action dated Dec. 12, 2019 in corresponding Brazilian Application No. BR112017004414, 6 pages.
Canadian Office Action dated Jan. 24, 2020 in corresponding Canadian Office Action No. 2,956,322, 8 pages.
Author Unknown, "3M Surface Pre-Treatment AC-131 Technical Datasheet," Mar. 2013 pp. 1-2.
English Translation of First Notification of Office Action and Search Report dated Aug. 3, 2018 in corresponding Chinese Application No. 201580050187.9.
Snihirova et al., "Smart protective ability of water based epoxy coatings loaded with CaCO3, microbeads impregnated with corrosion inhibitors applied on AA20224 substrates," Electrochimica Acta, 2012, 83, 439-447.
2, 5-dimercapto-1, 3, 4-thiadiazole information. Alfa Aesar, https://www.alfa.com/en/catalog/A12615/. As view on Apr. 10, 2018.
Danehy et al., "The oxidation of organic divalent sulfur by iodine. II. The equilibrating Thiod-Iodine-Disulfide-Hydrogen Iodide System in Acetic Acid and Evidence for Sulfenyl Iodide Intermediates," Journal of Organic Chemistry, 1971, 36, pp. 2525-2530.
2-mercaptobenzothiazole information. Chemicalland21. http://www.chemicalland21.com/specialtychem/perchem/2-MERCAPTOIBENZOTHIAZOLE.htrm. As viewed on Apr. 10, 2108.
Communication pursuant to Article 94(3) EPC dated Apr. 16, 2019 in corresponding European Patent Application No. 15 774 831.0, 4 pages.
VANLUBE product sheet, downloaded from http://www.ichemistry.cn/cas/VANLUBE on Aug. 28, 2014, 1 page.
Chemical Book 5,5'-dithiodi-1,3,4-thiadiazole-2(3H)-thione product sheet, 2 pages.
Jun, Yang et al. "Developements of polyurethane and epoxy abrasion-resistant anti-corrosive coatings and performance comparisons thereof", American Chemical Society, 2006, vol. 9, No. 5, pp. 18-21.
Nikonorov, E. M. et al. "Solid lubricating coatings with corrosion inhibitors" American Chemical Society, vol. 10, 1983, pp. 15-17.

* cited by examiner

COMPOSITIONS AND COATINGS WITH NON-CHROME CORROSION INHIBITOR PARTICLES

CROSS-REFERENCE TO RELATED APPLICATIONS

This application is a divisional of Ser. No. 14/852,065 filed Sep. 11, 2015, now allowed, which claims the benefit of U.S. Provisional Patent Application Ser. No. 62/055,939, filed Sep. 26, 2014, the entireties of both of which applications are incorporated herein by reference.

FIELD

Disclosed herein are descriptions that relate generally to corrosion inhibiting particles, such as core-shell particles, and in particular to corrosion-inhibiting particles that can be used in compositions and coatings for corrosion control of metals.

BACKGROUND

Corrosion is defined as the chemical or electrochemical reaction between a material, usually a metal, and its environment that produces a deterioration of the material and its properties. Corrosive attack begins on the surface of the metal. The corrosion process involves two chemical changes. The metal that is attacked or oxidized undergoes an anodic change, with the corrosive agent being reduced and undergoing a cathodic change. The tendency of most metals to corrode creates a major maintenance challenge for metals and metal products, particularly in areas where adverse environmental or weather conditions exist.

Chromium-based anti-corrosive systems containing hexavalent chromium compounds have proven to be an extremely useful and versatile group of chemistries that are extensively used in aircraft metal treatment processes. They impart many beneficial anti-corrosive characteristics to metallic substrates on which they are applied and have been used extensively for the pre-treatment of metals before coating, adhesive bonding and surface finishing. Chemically, chromium-based anti-corrosive systems have involved the combination of hexavalent chromium (e.g., $CrO_3$, $CrO_4^{-2}$, $Cr_2O_7^{-2}$) and hydrofluoric acid (HF) in the case of aluminum and its alloys. The hydrofluoric acid removes oxide film from the surface of the metallic substrate (e.g., aluminum) and the hexavalent chromium reacts with the exposed metal and a trivalent chromium oxide precipitates. Using aluminum as an example: $Cr_2O_7^{-2} + 2Al^0 + 2H^+ \rightarrow Cr_2O_7.H_2O + Al_2O_3$.

Chromium oxide, such as that produced according to the above reaction, is quite useful in anti-corrosive applications. It is quite stable in alkaline environments, it is water repellant (hydrophobic) and may act as a barrier coating towards water. Finally, it exhibits a "self-healing effect"—that is, residual hexavalent chromium in the coating may react with damaged areas of the coating—thereby producing more trivalent chromium oxide at damaged sites and therefore "healing" itself. Consequently, chromium-based, and in particular hexavalent chromium-based systems have been extensively used in the aircraft industry because they have proven to be: highly effective at reducing corrosion and as an adhesion promoter for organic coatings and adhesives; particularly resilient as the application/treatment process exhibits a low sensitivity towards variation in process conditions; extremely effective on aluminum alloys; and ensure considerable quality control characteristics as a skilled worker may tell the amount of chromium on the surface of a substrate by mere inspection (color) of the coating.

Concern about chromium—and in particular, hexavalent chromium—in the environment has generated a need to replace chromium-based systems. Therefore "environmentally friendly", commercially acceptable alternative to chromium-based systems are a welcome addition to corrosion prevention coatings.

SUMMARY

Disclosed is a corrosion inhibiting particle. The corrosion inhibiting particle may be usable in a sol gel coating for a pre-treatment or conversion coating alone or in combination with additional epoxy or olefin resin coating. The particle may include a core and a protectant. The core may include a water soluble corrosion inhibitor. The protectant may be disposed on at least a portion of a surface of the core and may be covalently or ionically bonded to a thiol group of the corrosion inhibitor. The protectant may be configured to reduce reaction between the core and the epoxy resin or the olefin resin.

Also disclosed is a method for preparing a corrosion-inhibiting particle. The method may include forming a core and forming a protectant on at least a portion of the core. The core may include a water soluble corrosion inhibitor. The protectant may be formed on at least a portion of the core by covalently or ionically bonding at least one of a reactive component of a protectant-forming fluid to a thiol group of the corrosion inhibitor.

Additionally, disclosed is an article that includes a metal substrate and a corrosion-inhibiting coating disposed on the substrate. The corrosion-inhibiting coating may include a corrosion-inhibitor particle incorporated in an epoxy and/or olefin or sol-gel based coating. The corrosion-inhibitor particle may include a core and a protectant disposed on at least a portion of a surface of the core. The core may include a corrosion inhibitor. The protectant may be covalently or ionically bonded to a thiol group of the water soluble corrosion-inhibitor. The protectant may be configured to reduce reaction between the core and the epoxy or the olefin.

The present disclosure is also directed to a method for preparing a non-chrome corrosion inhibitor coating composition. The method comprises providing a thiol-containing, chemically reactive corrosion-inhibitor. The corrosion inhibitor is micronized to form particle cores having a particle size in a range of about 100 nm to about 5 μm. The particle cores are incorporated into a coating composition.

The particles, compositions and coatings disclosed herein may be used for providing corrosion protection and durability for articles such as components of an airplane.

Additional advantages will be set forth in part in the description which follows, and in part will be understood from the description, or may be learned by practice thereof. The advantages will be realized and attained by means of the elements and combinations particularly pointed out in the appended claims.

It is to be understood that the foregoing general description and the following detailed description are exemplary and explanatory and are not restrictive of that which is claimed.

The accompanying drawings, which are incorporated in and constitute a part of this specification, illustrate examples and together with the description, serve to explain the principles of that which is described herein.

BRIEF DESCRIPTION OF THE DRAWINGS

FIGS. 6A-6B includes microscope images of non-chrome corrosion-inhibiting particles.

FIGS. 7A-7C are images of 2024 T3 Aluminum test panels coated with various corrosion-inhibiting particles at 4% w/v in 6% v/v of reactants in AC-131 (3M™ Surface Pre-Treatment AC-131).

DETAILED DESCRIPTION

Reference will now be made in detail to the present descriptions, examples of which are illustrated in the accompanying drawings. Wherever possible, the same reference numbers will be used throughout the drawings to refer to the same or like parts.

Notwithstanding that the numerical ranges and parameters setting forth the broad scope of the descriptions are approximations, the numerical values set forth in the specific examples are reported as precisely as possible. Any numerical value inherently contains certain errors necessarily resulting from the standard deviation found in their respective testing measurements. Moreover, all ranges disclosed herein are to be understood to encompass sub-ranges subsumed therein. For example, a range of "less than 10" can include sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following is described for illustrative purposes with reference to the Figures. Those of skill in the art will appreciate that the following description is exemplary in nature, and that various modifications to the parameters set forth herein could be made without departing from the scope of the present disclosure. It is intended that the specification and examples be considered as examples. The various descriptions are not necessarily mutually exclusive, as some descriptions can be combined with one or more other descriptions to form combined descriptions.

Figure 1:
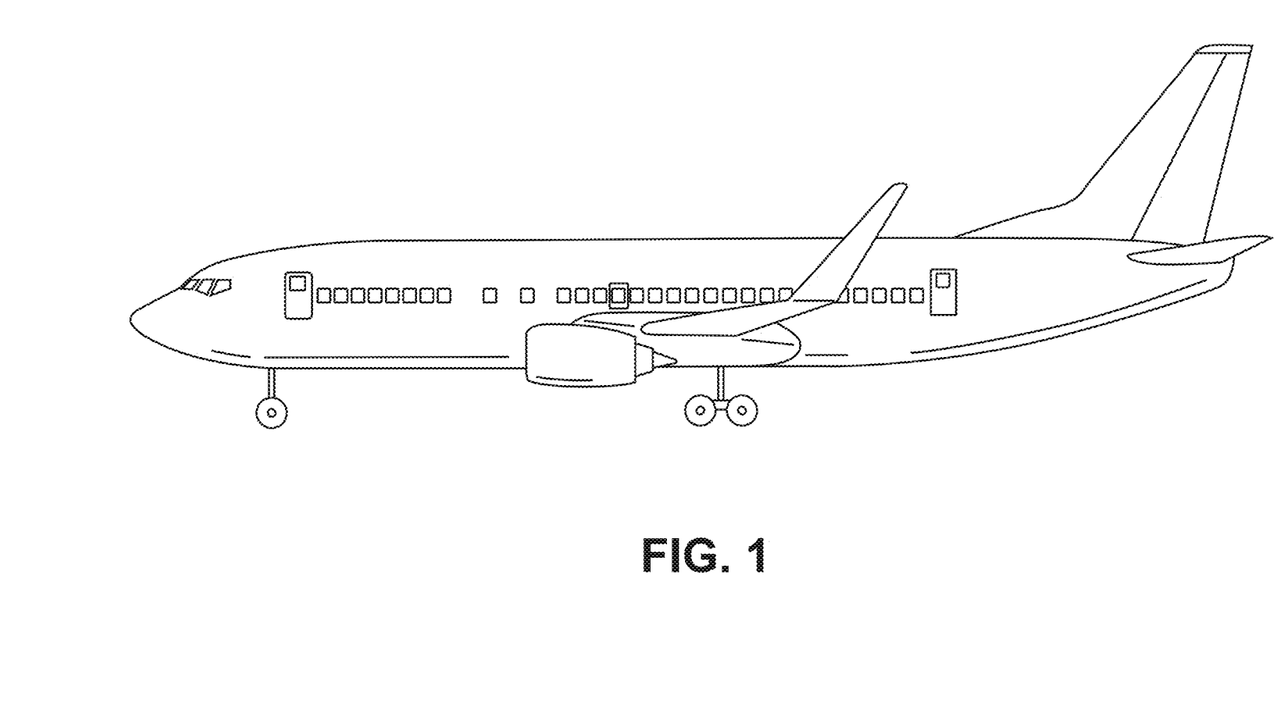
FIG. 1 illustrates one example of an aircraft.
Figure 2A:
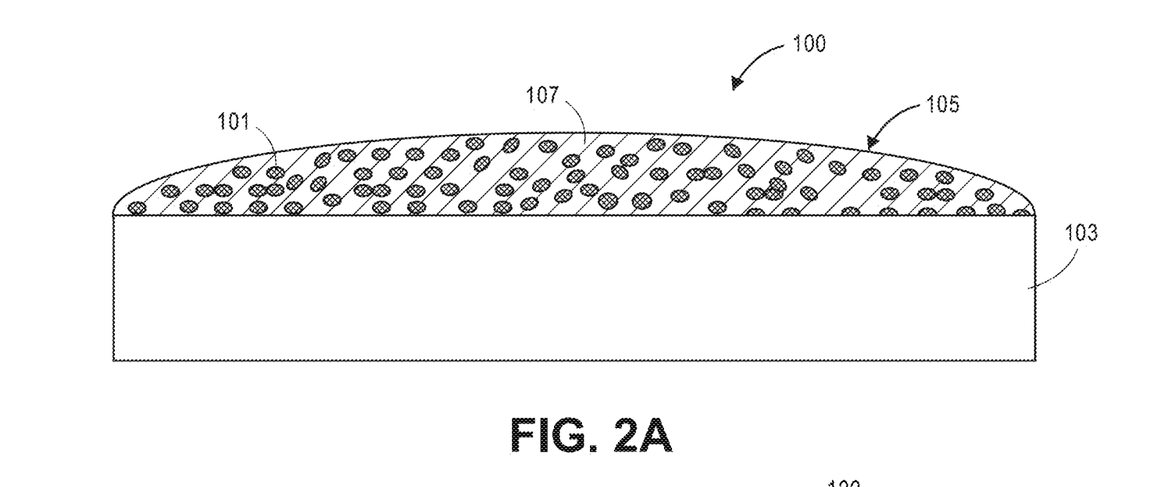
FIG. 2A illustrates an uncured coating composition that includes a corrosion inhibiting particle and at least one of an epoxy and/or olefin resin or sol-gel coating with the uncured coating composition disposed on a substrate.
Figure 2B:
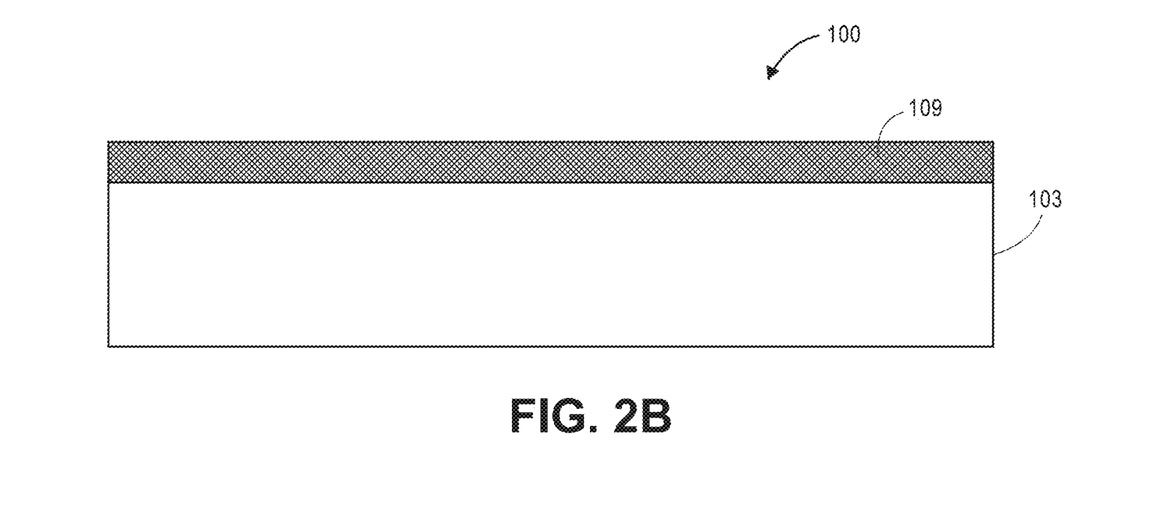
FIG. 2B illustrates the coating formulation of FIG. 2A after curing on the substrate.

Articles, such as metal surfaces that are subject to environmental corrosion, in particular to oxidative corrosion, such as those of an aircraft shown in FIG. 1, can be protected against such corrosion. A metal surface of such an article may be protected by treating with corrosion inhibiting particles, such as those included in a corrosion-inhibiting coating formed from a corrosion-inhibiting coating composition. For example, as shown in FIGS. 2A-2B, a corrosion-inhibiting coating 109 can be formed on a surface of substrate 103, which may be a metal, of article 100. An exemplary metal for substrate 103 comprises aluminum and aluminum alloys, steel, magnesium and magnesium alloys, copper and copper alloys, tin and tin alloys, nickel alloys and titanium and titanium alloys. The corrosion-inhibiting coating 109 can be formed from a corrosion-inhibiting coating composition 105 that includes a corrosion-inhibiting agent 101, such as a non-chromium-based corrosion inhibiting particle. The corrosion-inhibiting agent 101 may be incorporated with a corrosion-inhibiting coating composition 105 that includes a matrix 107, such as a resin, for example an epoxy (in the case of coatings for an airplane's interior), an olefin, such as polyurethane (in the case of coatings for an airplane's exterior), both the epoxy and the olefin (in the case of multilayer coatings used for both internal and external purposes), and an epoxy or olefin and sol-gel coating system (in case of coating for an airplane's exterior). The matrix 107 may be a thermoplastic polymer such as polyvinylbutyral.

Figure 3:
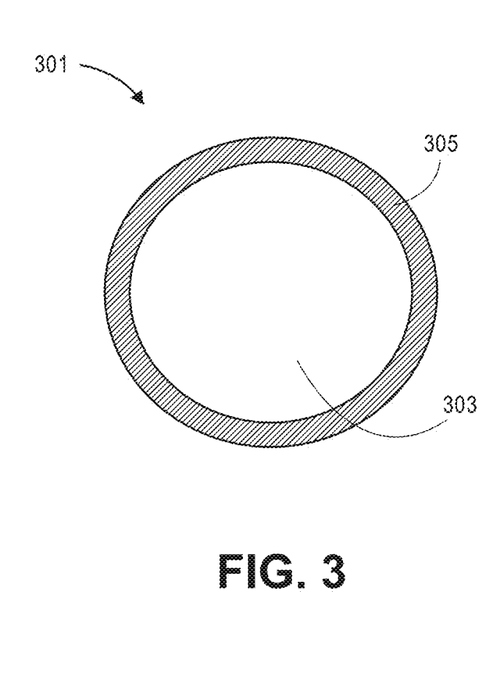
FIG. 3 illustrates a corrosion inhibiting particle having a protectant disposed on a surface of the corrosion inhibiting particle's core.

Corrosion-inhibiting agent 101, as described above, may be the corrosion-inhibiting particle 301 illustrated in FIG. 3. Corrosion-inhibiting particle 301 may be an organic or inorganic compound that imparts corrosion resistance to a metal when at least a portion of it is dissolved. For example, the particle may include an insoluble thiol or sulfide containing organic molecule. The particle may include a core 303 formed of, for example, a corrosion inhibitor, such as a water soluble corrosion inhibitor. To form the coating composition that includes the corrosion-responsive agent and the epoxy, as described above, the corrosion-responsive agent may be transported in a solvent. In the case that the corrosion-responsive agent described above, is a corrosion-inhibiting particle, the particle may be reactive. That is, the corrosion inhibitor of the corrosion-inhibiting particle's core may be reactive. For example, if the corrosion inhibitor reacts undesirably during the formation of a cured coating, the corrosion-inhibiting properties may be consumed and unable to provide protection against corrosion. Thus, the corrosion-inhibiting particle 301 may also include a protectant 305 disposed on at least a portion of a surface of the core. In other words, the core 303 may include a corrosion inhibitor and the protectant may be configured to reduce reaction between the core and an epoxy or olefin resin, for example, the epoxy or olefin resin matrix of corrosion-inhibiting coating composition 105. In an example, the protectant may be configured to reduce cross-linking between the core and the epoxy resin or the olefin resin matrix. The protectant may be water-permeable so as to allow water to reach the core and dissolve the corrosion-inhibitor to form a dissolved corrosion-inhibitor. The protectant may also be configured to allow for the diffusion of dissolved corrosion-inhibitor through the protectant.

The core may have a size in a range from about 100 nm to about 5 µm, for example, from about 100 nm to about 1 µm. As described further below, the core may be a micronized core. That is, core 303 may be attained by reducing the particle size of a crude particle, such as via micronizing. In an example, particle size may be reduced by air-milling of a synthesized or commercially purchased, crude non-chrome corrosion inhibitor. As used herein, the term "non-chrome" refers to materials that are chromium free, for example, they may not include chromium (VI).

The corrosion inhibitor may be a polydisulfide, such as a mercaptan-terminated polysulfide of dimercaptothiadiazole (DMcT). Micronizing or reducing crude particle size, for example, by milling the crude corrosion inhibitor, may be performed to enrich reactive groups, such as the thiol functional groups of the mercaptan-terminated chains of the polydisulfide corrosion inhibitor, on a surface of a particle core. The polydisulfide may be represented by formula I:

(I)

where n is 1 or 2, and polymers thereof.

The protectant 305 may be disposed on at least a portion of the surface of core 303. For example, the protectant 305 may encapsulate the core 303 forming a shell surrounding the core. The protectant 305 may be covalently bonded to the core. For example, as described further below, the protectant may be covalently bonded to a thiol functional group extending from the core, such as extending from the core's surface. Accordingly, the protectant formed on a surface of the core may be viewed as a core-shell corrosion-inhibiting particle.

In one example, the core is configured with its surface enriched with the thiol functional groups of the thiol-terminated corrosion-inhibitor. Enrichment may be performed by reducing the particle size, such as via micronizing crude corrosion-inhibitor material. A reactive-group of a protectant-forming material, such as the epoxy ring of an epoxide protectant-forming material, may react with the thiol group, thus covalently bonding the protectant-forming material to the thiol groups to form the shell. Accordingly, the shell may be covalently bonded to the core.

The micronized core may be introduced directly to a corrosion-inhibiting coating composition. Thus, thiol groups enriched on the surface of the micronized core may react with a component of a corrosion-inhibiting coating composition, for example, an epoxy of the coating composition, without forming a discrete shell over the core. This may preserve other portions of corrosion-inhibitor in the core, such as internal corrosion-inhibitor in the core that does not extend to the surface of the core. Thus, corrosion-inhibitor not extending to the surface of the core and located within the core may remain free to perform corrosion-inhibiting function even after the coating composition is cured.

The micronized core may be introduced directly to a corrosion-inhibiting coating composition that includes a protectant-forming material portion, such as a protectant-forming fluid, and a matrix portion. The protectant-forming fluid and a matrix portion of the composition may be the same type of material. Thus, the protectant-forming material may include a first portion and the matrix material may be considered a second portion of the protectant-forming material. Micronized core particles with enriched surfaces comprising functional groups, such as thiol functional groups as described above, may be placed in contact with the protectant-forming fluid. At least the first portion of the protectant-forming material may react with the surface functional groups of the micronized particles to form a protectant on at least a surface of the core, thereby forming core-shell corrosion-inhibiting particles. The second portion of the protectant-forming material may not react with the functional groups on the micronized cores, and may remain as the matrix material for the coating formed from the coating composition in which the core-shell particles are dispersed.

The protectant disposed on a surface of the core may be capable of reacting with the matrix material of the coating composition, such as a matrix 107, which may include a cross-linking agent. Accordingly, protectant 305, such as a shell covalently bonded to the core, may be viewed as a sacrificial component. For example, protectant 305 may react with the surrounding environment during processing to preserve the corrosion-inhibitor in the core 303, and reduces reaction between the corrosion inhibitor and the surrounding environment of cross-linkable material in the matrix. The micronized core of the particles described herein may be functionalized by neutralization of the corrosion inhibitor. This neutralization step provides for improved adhesion of a coating that includes the particles described herein to a substrate, for example, a metal substrate, on which it is applied.

The surface of the core may be enriched, for example, via micronizing a crude corrosion inhibiting particle, with at least one functional group of the corrosion inhibitor. The functional group may have the formula X or —R—X, where X is selected from, for example, a mercapto (i.e., —SH or thiol) and may be linked to the corrosion inhibitor of the core by R, which may be an alkyl chain, such as a lower alkyl ($C_1$-$C_6$) chain, an alkyl ether group or an alkyl amine group. Accordingly, the functional group may have the formula —$(CH_2)_n$—SH, where n may be an integer selected from the range that includes from 0 to 6, for example, from 1 to 6, such as from 0 to 3. As used herein, the term "alkyl" may refer to a straight or branched chain saturated cyclic (e.g., cycloalkyl) or acyclic hydrocarbon group of from 1 to 12 carbons. Alkyl groups may include $C_1$-$C_8$, $C_1$-$C_6$, $C_1$-$C_8$, $C_2$-$C_7$, $C_3$-$C_{12}$, and $C_3$-$C_6$ alkyl. Specific examples include methyl, ethyl, 1-propyl, 2-propyl, 2-methyl-1-propyl, 1-butyl, 2-butyl, and the like. Alkyl groups, used in any context herein, may optionally be substituted with halogen, amino or sulfyl groups, or may include one or more heteroatoms in the alkyl chain, such as oxygen (an ether) or nitrogen (an amine).

Figure 4:
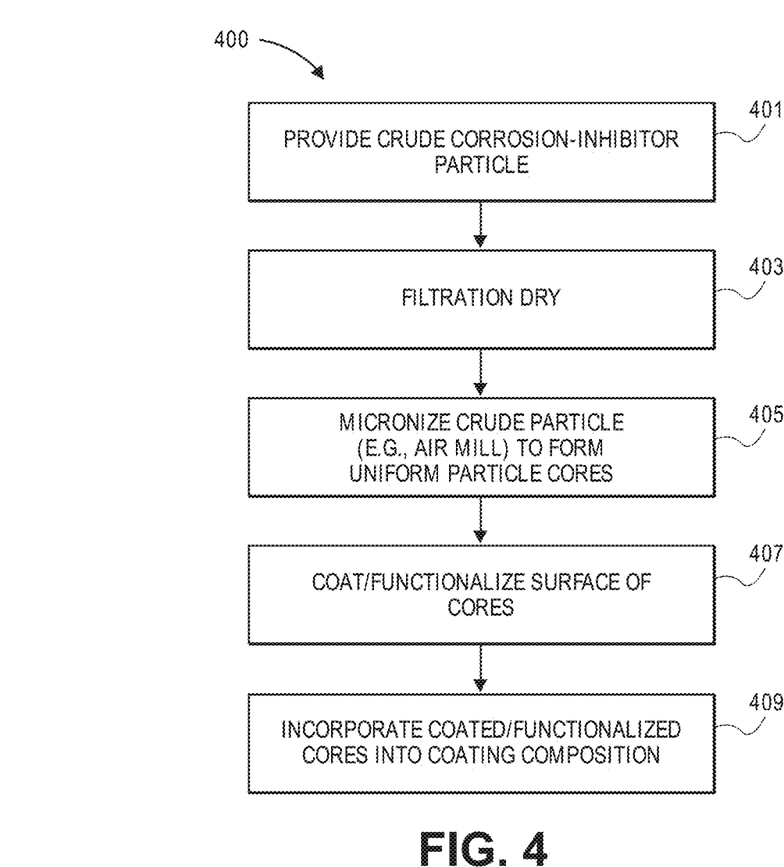
FIG. 4 is a flowchart depicting a method of making a corrosion inhibiting particle and corrosion inhibiting composition.

FIG. 4 includes a flow-chart 400 that illustrates a method for forming a corrosion inhibiting particle, such as corrosion-inhibiting particle 301, and for forming a corrosion-inhibiting composition, such as a corrosion-inhibiting composition 105. Generally, in such a method for preparing a corrosion inhibiting particle, a core comprising a corrosion inhibitor, such as core 303, is formed. Additionally, a protectant, such as protectant 305 is formed on the surface of the core. The protectant may be formed by covalently or ionically bonding at least one of a reactive component of a protectant-forming composition to the corrosion inhibitor.

Figure 5A:
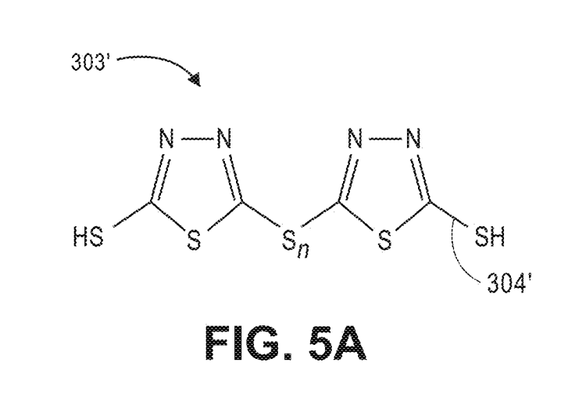
FIG. 5A is an organic structure of a corrosion-inhibitor.

At 401, a crude corrosion inhibitor particle is provided. The crude corrosion inhibitor particle may be synthesized according to known methods such as those described for "unprotected" corrosion inhibitor particles as in Comparative Example 4 and Comparative Example 5 described below, which are based on synthesis procedures disclosed in U.S. Pat. No. 4,599,425 granted on Jul. 8, 1986 and U.S. Pat. No. 4,107,059 granted on Aug. 15, 1978, respectively. Preparation of a corrosion inhibitor may include precipitation of an insoluble species, such as by dissolving a compound in an organic solvent and then precipitating the corrosion inhibitor out of solution by adding the dissolved compound into a non-solvent. For example, a compound such as bis-DMcT may be dissolved in an organic solvent such as THF, and the dissolved bis-DMcT may be added to water to precipitate a crude corrosion inhibitor particle. Alternatively, crude corrosion inhibitor particle may be derived from VANLUBE® 829 (available from Vanderbilt Chemicals, LLC, Norwalk, Conn.), or INHIBICOR® 1000 (available from Wayne Pigment Corporation, Milwaukee, Wis.), or a combination of both. An organic structure of a representative crude corrosion inhibitor is shown in FIG. 5A as organic structure 303', and includes mercaptan-terminated chains 304'.

Figure 5B:
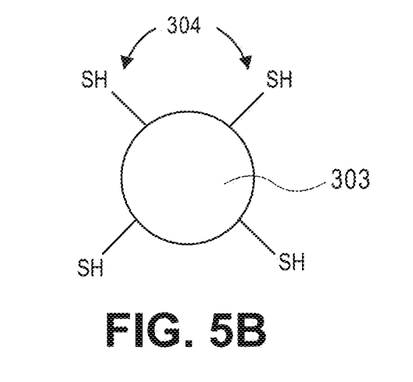
FIG. 5B illustrates a micronized core, the surface of which is enriched with mercaptan-terminated chains of a corrosion inhibitor.

Returning to FIG. 4, the crude corrosion-inhibitor particle may be filtration dried at 403. At 405, particle core, such as core 303 is formed by micronizing the crude corrosion inhibitor particle to a size, such as predetermined size, of about 0.1 µm to about 5 µm, for example, 0.1 µm to about 5 µm using a suitable micronization process. For example, crude corrosion-inhibiting particle can be processed via air mill or other micronizer. While not limited to any particular theory, it is believed that micronizing the crude corrosion-inhibitor exposes functional groups of the corrosion-inhibitor, such as mercaptan-terminated chains 304', thereby enriching a surface of the core 303 with functional group 304 as shown in FIG. 5B. Optionally, because micronizing the particles exposes functional groups of the corrosion-inhibitor, in some cases, micronizing results in particles having acidic character (i.e., lower pH than crude, unmicronized particles of larger size). Therefore, after or during micronizing, the corrosion-inhibiting particles may be neutralized such that surface charges provided by the exposed groups (for example newly exposed SH groups, wherein S has a negative charge and H has a positive charge), are neutralized. In one example, the neutralization may be achieved by exposing the particles to a base, such as NaOH or KOH, during or after micronization of the particles. A similar result may be achieved by coating the particles (i.e., covalently bonding the particles), thereby forming a chemically neutral shell that protects the core from reacting with a resin or sol-gel in which they are disposed when formulating a corrosion-inhibiting coating. In other words, such neutralization to form a chemically neutral shell protects the free-thiol groups described below.

Figure 5C:
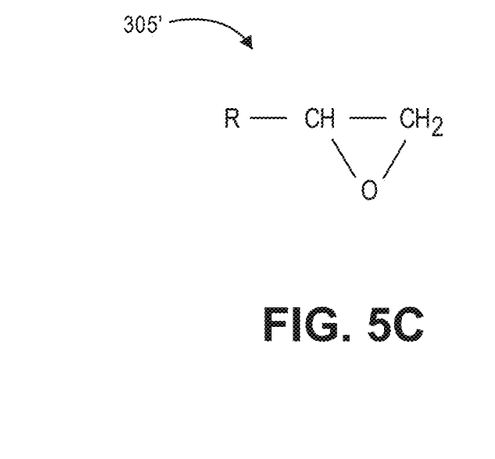
FIG. 5C is an organic structure of an epoxy which may be used as a protectant-forming composition, a matrix material of a coating composition, or both.

Returning to FIG. 4, uniform ones of the micronized cores having a predetermined size in the range of about 0.1 µm to about 5 µm, for example, 0.1 µm to about 1 µm may be selected for further processing. For example, at 407 a protectant may be formed via coating and/or functionalizing a protectant material to a surface of the cores. To coat and/or functionalize a surface of the core, the micronized core may be introduced into a fluidizer in which a coating material sprayer provides a protectant-forming composition that includes, for example, an epoxy. An organic structure 305' representative of an epoxy is shown in FIG. 5C.

In an example, the functional group 304 of the corrosion-inhibitor of core 303 may react with a reactive component of a protectant-forming composition, such as an epoxy ring, to form the corrosion-inhibiting particle that includes a core 303 with a protectant disposed on the core. That is, in a fluidizer, a fluidized bed may be formed that contains the micronized core and the protectant-forming composition, such as an epoxy, which can react with a surface group, such as an —SH (i.e., thiol) group of the corrosion inhibitor. The protectant may, therefore, functionalize to a surface of the core. In other words, the groups exposed on the surface of the core as a result of micronizing the crude corrosion inhibitor may react with a surrounding protectant-forming material, such as at least one of an epoxy resin. In the case of a core comprising a mercaptan-terminated polysulfide of dimercaptothiadiazole corrosion-inhibitor, a reactive component of the protectant-forming composition reacts with the "free" —SH (thiol) on the particle surface, via, for example, formation of a covalent bond therewith, and forms a protectant that may surround the core. In an example, the protectant covalently bonded to the core forms a shell that surrounds the core. In an example, the protectant encapsulates the core. Alternatively, the micronized cores may be immersed in an organic solution of epoxy followed by solvent removal.

As discussed above with respect to FIGS. 2A-2B, at 409 the corrosion-inhibiting particles that include a core and a protectant disposed on the core may be incorporated into a coating composition, such as a paint/coating formulation as at 409 in FIG. 4. The coating formulation may then be applied to a substrate followed by air-drying and/or UV curing to form a corrosion-inhibiting coating. Such a coating may be permeable to allow water to diffuse therein. Additionally, such water may diffuse across the protectant, such as a protectant that is water-permeable, in order to reach particle's core. Upon reaching the particle's core, the water may dissolve the corrosion-inhibitor which can then subsequently diffuse out and reach a coating defect site and absorb to exposed underlying metal substrate, thereby inhibiting corrosion of the substrate. It is noted that the corrosion-inhibitor core of the corrosion-inhibiting particle may be coated with a controlled release protectant. For example, the protectant may be a water soluble coating or a pH sensitive coating such as poly(meth)acrylates used in pharmaceutical applications, for example, EUDRAGIT® acrylic polymers available from Evonik Industries, AG, Essen, Germany. Thus, in the case of a water-soluble protectant, upon contacting water, the water-soluble protectant dissolves thereby releasing the corrosion-inhibitor from the core. In the case of a pH sensitive protectant, the protectant may dissolve or becomes permeable in acid or basic aqueous environments encountered in corrosion processes, thereby releasing the corrosion inhibitor of the core.

Figure 5D:
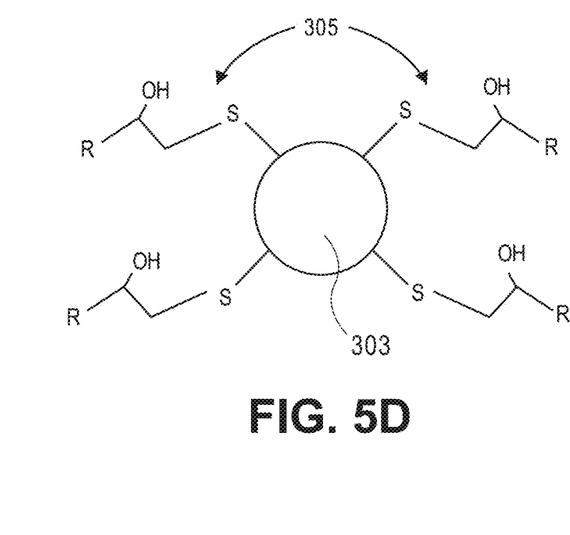
FIG. 5D is a close-up view of a corrosion-inhibiting particle that includes a core and a protectant covalently bonded to the corrosion-inhibitor of the core.

As shown in FIG. 5B, core 303 may be enriched with functional group 304, such as a thiol-terminated end group of the corrosion inhibitor. The thiol-terminated end group may react with a material such as a component, for example organic structure 305', of a protectant-forming composition, to at least partially cover the surface of core 303, as in FIG. 5D. Such coverage may protect the core's corrosion inhibitor, for example, when the particle is incorporated in a matrix of a coating composition that includes a cross-linkable resin. Exemplary cross-linkable resins in such coating compositions include aliphatic amine-cured epoxies, polyamide epoxy, polyamine adducts with epoxy, kerimine epoxy coatings, aromatic amine-cured epoxies, silicone modified epoxy resins, epoxy phenolic coatings, epoxy urethane coatings, coal tar epoxies, oil-modified polyurethanes, moisture cured polyurethanes, blocked urethanes, two component polyurethanes, aliphatic isocyanate curing polyurethanes, polyvinyl acetals and the like, ionomers, fluorinated olefin resins, mixtures of such resins, aqueous basic or acidic dispersions of such resins, or aqueous emulsions of such resins, and the like. Methods for preparing these polymers are known or the polymeric material is available commercially. It should be understood that various modifications to the polymers can be made such as providing it in the form of a copolymer.

The corrosion-inhibiting coating may be formed from a composition formed of a mixture of at least two components, such as an epoxy (component A) and a hardener (component B). Accordingly, component A, component B, or each of components A and B may include the corrosion inhibiting particles comprising the core and protectant disposed on at least a surface of the core as described above. Alternatively, the coating composition may additionally include a separate source of the corrosion inhibiting particles (component C) which may be mixed with either one or each of component A and component B so long as the coating composition includes the corrosion inhibiting particles described above, and a carrier, for example, at least one of an uncured epoxy resin and an uncured olefin resin.

The formulation that is used in forming the corrosion-inhibiting coating may be applied to a substrate by an appropriate coating method, such as dip coating, spin coating, and spray coating.

In addition to the corrosion-inhibiting particle and cross-linkable resin, coating formulations can contain other materials. For example, any plasticizer, colorant, curing catalyst, residual monomer, surfactant, or any other material that adds useful properties to the coating, or at least does not reduce the functionality of the coating, can be included in the coating in amounts that are known to those of skill in the art of polymer compounding.

It is believed that the present methods can be used to prevent or reduce corrosion for any corrodible metal. The methods and compositions are particularly useful on steel and aluminum alloys, and more particularly on aluminum/copper alloys. For example, the aluminum/copper alloys are those that comprise at least 1% by weight copper, such as aluminum/copper alloys that contain at least 4% by weight copper, for example, copper-containing aluminum alloys AA2024 and AA7075.

EXAMPLES

Example 1—Preparation of Crude Corrosion Inhibiting Particles from VANLUBE® 829

Crude corrosion inhibitor having a composition that includes a structure represented by formula (II) was derived from VANLUBE®829 available from Vanderbilt Chemicals, LLC.

Example 2—Particle Size Reduction of VANLUBE® Corrosion Inhibitor, Dispersion of Reduced-Particle-Size VANLUBE® 829 Corrosion Inhibitor into Solvent Based Sherwin Williams Polyurethane Primer CM0480, Formation of Protectant Via Reaction of Corrosion Inhibitor with Polyurethane, and Formation of Corrosion-Inhibiting Coating for Use on E 41 Sample Series Substrates Particle size reduction to enrich the particles' surfaces with functional groups and dispersion of dry VANLUBE® 829 in Sherwin Williams JetFlex Reducer/thinner CM0110845 was carried out by combining 1.50 g VANLUBE® 829 with 4.0 mls CM0110845 reducer with 5.0 mls of 2 mm glass beads in a 60 ml plastic bottle and subjecting it to 20 minutes of mixing at 750 rpm on a Thinky planetary mixer. The 60 ml plastic bottle was initially wrapped with a sufficient amount of ⅛" thick AP/Armaflex insulation tape to prevent it from spinning inside the holder of the Thinky mixer. An additional 4.0 mls of CM0110845 reducer was added to the mix bottle to decrease the paste-like viscosity of the VANLUBE®/reducer mixture following the 20 minute mixing period.

A 14.00 g portion of Sherwin Williams polyurethane primer was combined with with 2.00 g Sherwin Williams primer catalyst CM0120930 and 4.0 mls CM0110485 reducer in a 60 ml plastic bottle and mixed for 20 minutes at 750 rpm on a Thinky planetary mixer for initial mixing of the primer binder components. Following this initial mixing of the primer binder, the mixture of dispersed VANLUBE® 829 in CM0110485 reducer was added to the primer binder mixture. Core-shell corrosion-inhibiting particles were formed via reaction of surface functional groups enriched on the surface of the reduced-particle-size VANLUBE® 829 corrosion inhibitor with the polyurethane. Two additional 1.0 ml portions of CM0110485 reducer was added to the VANLUBE® 829 dispersion bottle to help rinse out glass beads and VANLUBE® residues on the inside walls of the container and then added to the primer. The combined primer and VANLUBE® 829 inhibitor components were then given a final 20 minute mix at 750 rpm on the Thinky mixer before straining it through a paper paint filter to remove the glass beads. The remaining portions of the polyurethane primer that did not react to form a protectant on the corrosion inhibitor formed a matrix in which the core-shell corrosion-inhibiting particles were dispersed and the dispersion was collected in an airbrush reservoir prior to spray application to substrates.

Example 3—Forming Corrosion-Inhibiting Composition and Coating

The corrosion-inhibiting particle of Example 2 was introduced into a paint (i.e., coating) formulation. The coating formulation was applied to a substrate and air dried or UV cured.

Example 4—Use of a Disulfide/Dithiol Compound to Increase Corrosion Resistance of Aluminum and its Alloys A 1% solution of 5,5-dithiobis-(1,3,4-thiadiazole-2(3H)-thione) was made up of VANLUBE® 829 in deionized water. This mixture was processed on a paint shaker using glass beads to help incorporate the VANLUBE® into the water. A high speed shear mixer or a centrifugal planetary mixer would have worked as well. The VANLUBE® did not dissolve, but a portion was reduced to nano-sized particles which stayed in suspension.

2024-T3 aluminum panels (3"×6"×0.032") were used as test specimens. Three of these panels were chromium conversion coated to use as controls. Three panels were put through an aluminum cleaning processing line (solvent wipe, alkaline clean and deoxidized) prior to immersion in the 1% solution. Immersion time was 5 minutes at room temperature. These panels were then rinsed. Three panels were wet abraded with Scotch-Brite 7447 pads, rinsed and allowed to dry. The 1% solution was then spray applied to the panels. The panels were kept wet with the solution for 2 minutes at room temperature. These panels were then allowed to air dry. Three panels were solvent wiped only to use as control panels.

All the panels were then placed into neutral salt spray per ASTM B-117 for testing. After 4 hours of exposure the chromium panels were unaffected. The panels which had been abraded, however, performed better than the immersed and rinsed panels or the bare unprocessed panels.

The use of a disulfide/dithiol compound (even in water), while not as effective as hexavalent chrome, improved the corrosion resistance of aluminum and its alloys.

COMPARATIVE EXAMPLES

Comparative Example 1: Preparation of Corrosion-Inhibiting Coating

Formulation That Includes Unprotected Corrosion-Inhibiting Particles.

Waterborne epoxy coating formulations containing varying amounts of unprotected VANLUBE® corrosion inhibitor and/or pigments and filler materials were prepared and tested for their ability to serve as corrosion resistant coatings on bare 2024 T3 aluminum substrates. Formulation were based on one listed in U.S. Pat. No. 8,114,206, granted on Feb. 14, 2012, which is incorporated by reference herein in its entirety. The binder for theses coatings consisted of EPI-REZ 6520-WH-53 resin and EPIKURE 6870-W-53 obtained from Momentive Specialty Chemicals. VANLUBE® 829 from Vanderbilt Chemicals, LLC was the principal corrosion inhibitor used in these coating, although a zinc oxide treated version of VANLUBE® 829 was also evaluated in one formulation. Additional pigments and fillers used in the formulations included Kronos 2310 TiO2, Alfa Aesar barium metaborate, Azco BC-1-20 wet ground mica and N-200 ceramic microspheres from Zeeospheres.

Comparative Example 2: Preparation of Corrosion-Inhibiting Coatings

Corrosion-inhibiting coatings were prepared from the coating formulations of Comparative Example 1. For example, some samples were prepared by spin coating 3"×3"×0.040" thick bare 2024 T3 aluminum substrates. Surface preparation for these early samples consisted solvent wiping to remove panel marking inks and hand washing with an ALCONOX® detergent solution until a water break-free surface was obtained. No de-oxidation step or further processing of the substrates with either ALODINE® (available from Henkel Corporation of Rocky Hilly, Conn., or BOE-GEL® (available from The Boeing Company, Chicago, Ill.) surface treatments was performed in order to limit potential corrosion rate influences strictly to formulation components. Coating samples for others of the formulations were prepared by spray application using an Iwata Eclipse airbrush, using 20 PSI triggered air pressure. Approximately 25 mls of coating solution was prepared for each formulation and was sufficient to coat nine 3"×3" panels using the Iwata airbrush, with coating solution left over. The resulting samples were allowed to air dry overnight and were then given accelerated cures at 160 F for at least 2 hours before performing any tests.

Comparative Example 3: Characterization of Corrosion-Inhibiting Coatings Formed from Formulations Containing Unprotected VANLUBE® 829 Corrosion-Inhibitor Physical properties of the water borne epoxy coating formulations containing a mixture of VANLUBE® 829, pigment and filler package at loadings levels as low as 15 PVC were poor, even those with low pigment loading level. Coating samples from formulations with 26 to 45 PVC loading levels were noticeably chalky when touched. During BSS 7225 Type 1, Class 3 dry tape adhesion tests, the tape readily pulled particles from the outer surface of the samples, while the rest of the scribed coating appeared to remain adhered to the panel surface. Although initially appearing to past the adhesion test, these coating were very easy to damage or remove from the substrate via scratching. Water resistance of such coatings was also poor.

Initially, the poor physical characteristics of the coatings were attributed to unknown oil absorption characteristics of the VANLUBE® 829 material that may have putting much higher wetting demands on the epoxy binder than had initially been thought. To test this assumption, coatings with progressively lower VANLUBE® 829 and pigment loading levels were prepared and tested. Reasonable physical properties were first obtained when VANLUBE® 829 was used alone as the sole pigment or filler material at loading levels of 5.9 PVC and 10 PVC. However, the addition of approximately 5 PVC of the pigment and filler materials to the 10 PVC VANLUBE® 829 coating formulation, weak coatings with poor strength and weak water resistance were produced.

The dramatic deterioration of coating physical properties at relatively low overall inhibitor and pigment loading levels indicated that VANLUBE® 829 might be reacting with either the epoxy resin component or cure agent of the waterborne coating system. The possible reaction of VANLUBE® 829 thiol groups with either the epoxy ring of the binder resin or amine groups of the cure agent may be a potential consequence of the addition of this corrosion inhibitor to epoxy coating systems.

To further investigate whether VANLUBE® 829 was interfering with the cure of the epoxy coating, vials containing amounts of the epoxy resin and cure agent normally used to prepare the waterborne coating samples were prepared and mixed, with and without the amount of VANLUBE® 829 used to prepare a 10 PVC coating. After 24 hours of aging in the sealed vials, the epoxy binder without VANLUBE® 829 had stiffened noticeably and developed a dryer texture. In contrast, the consistency of the epoxy binder that had been mixed with VANLUBE® 829 appeared to be unchanged, indicating possible interference by the added corrosion inhibitor with the cure of the coating. When this test was repeated using zinc-VANLUBE® instead of VANLUBE® 829, a very slight increase in coating viscosity was noticed after 24 hours. This result was interpreted as an indication that the less reactive zinc-VANLUBE® had a somewhat less detrimental effect on the cure of the epoxy coating system than the original VANLUBE® 829 material.

Comparative Example 4—Synthesis of bis-[2,5-dithio-1,3,4-thiadiazole] (BDTD)

Synthesis of bis-[2,5-dithio-1,3,4-thiadiazole] was performed according to the following synthesis scheme:

A corresponding procedure, similar to that disclosed in U.S. Pat. No. 4,599,425, was followed: 15 grams of DMCT (0.1 mole), FW=150.22, in the form of a powder was suspended in 200 ml of water at 0° C. While vigorously stirring the suspension, 14 grams of 30% hydrogen peroxide solution (corresponding to 0.1 mole) was added dropwise (using the peristaltic pump) at a slow rate such that the reaction temperature did not exceed 50° C. 1 hour after the addition of the peroxide, the BTDT was filtered off, washed three times with DI water and dried at 50° C. for 12 hours.

Comparative Example 5—Synthesis of poly(2,5-dithio-1,3,4-thiadiazole) (PDTD)

Synthesis of poly(2,5-dithio-1,3,4-thiadiazole) was performed according to the following synthesis scheme:

A corresponding synthesis procedure, similar to that disclosed in U.S. Pat. No. 4,107,059, was followed: 22 grams (0.1 mole) of dipotassium 1,3,4-thiadiazole-2,5-dithiolate KDMCT (0.1 mole) was dissolved in 200 ml of water at 20° C. 25.1 grams ammonium persulfate was dissolved in 120 ml water. While vigorously stirring the KDMCT solution, the persulfate solution was added dropwise with a peristaltic pump over a period of 45 minutes. The solution was stirred an additional hour (solids formed during this period). The resulting PDTD product was washed 4× with 200 ml water. The solids were transferred to a Waring blender, dispersed in 200 ml water and acidified with 0.1 M HCl to bring the pH to 2.0. The product was washed again with water (6×250 ml) and dried in a vacuum desiccator.

Comparative Example 6—Micronization and Neutralization of INHIBICOR® 1000

Figure 6A:
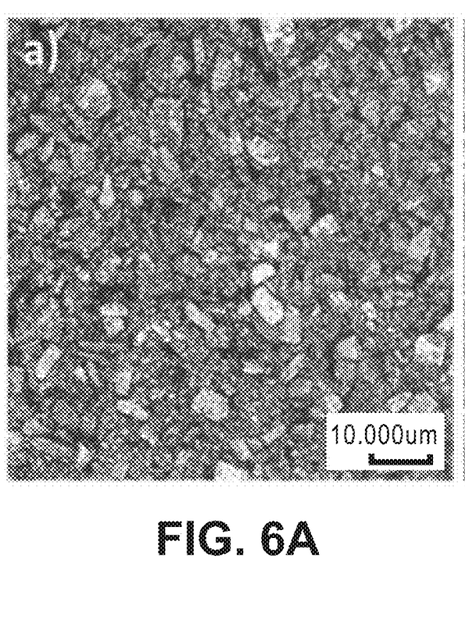
FIG. 6A shows larger, raw particles (i.e., before micronization)
Figure 6B:
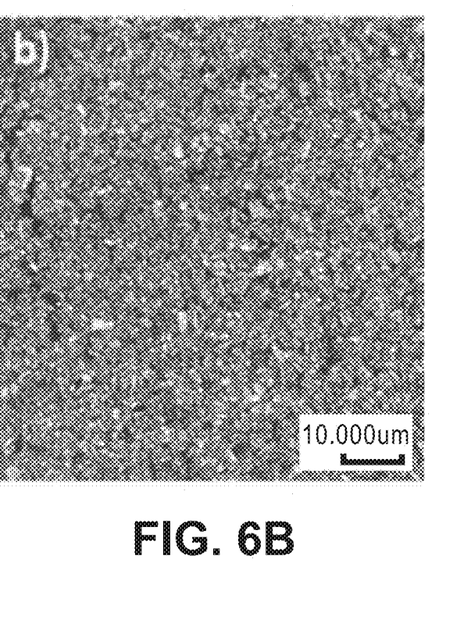
FIG. 6B shows that the smaller, micronized particles resulting from the micronizing of the particles of FIG. 6A.
Figure 7A:
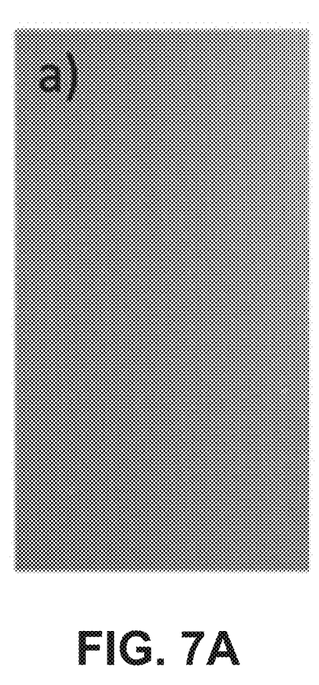
FIG. 7A shows a test panel coated with a coating that comprises non-micronized INHIBICOR®1000 particles.
Figure 7B:
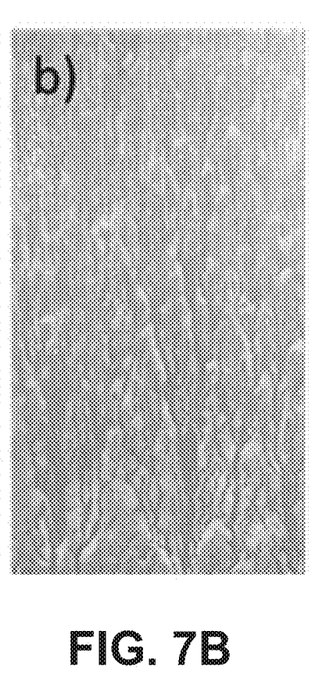
FIG. 7B shows a test panel coated with a coating that comprises micronized corrosion-inhibiting particles as described herein.
Figure 7C:
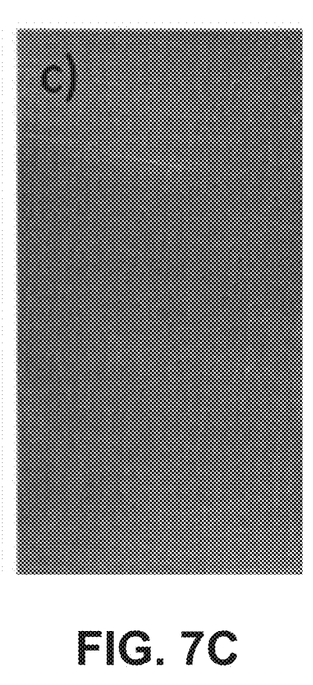
FIG. 7C shows a test panel coated with a coating that comprises micronized and neutralized particles according to the descriptions provided herein.

The particle size of INHIBICOR®1000 (available from WPC Technologies, Milwaukee, Wis.) was decreased from 3.49 µm (FIG. 6A) to 2.50 µm (FIG. 6B) using a Micronizer jet mill from Sturtevant. As shown in FIGS. 7A, 7B and 7C, non-micronized (as-is), micronized and INHIBICOR®1000 particles, were formulated in high strength AC-131 (4% w/v INHIBICOR®1000 in 6% v/v of (Si+Zr) in AC-131) and sprayed evenly on bare Al 2024 panels. The solubility of the INHIBICOR®1000 increased in the resin matrix as a result of the micronization, as observed for panels in FIGS. 7A-7B. However "river-like" patterns were observed on the panel (b) (FIG. 7B) due to poor adhesion of the coating. The poor adhesion of the coating was attributed to a drop in pH observed between non-micronized particles (6.35 pH) and micronized particles (5.63 pH). While not limited to any particular theory, it is believed that as a result of micronization, the newly exposed surfaces of micronized particles are enriched with reactive groups, such as —SH groups. As a result, it is believed that more negatively charged and positively charged atoms of the reactive groups (e.g., more negatively charged S atoms and positively charged H atoms on the surface of the micronized particles) provide for a lowering of the pH in an aqueous mixture as compared to non-micronized particles also in an aqueous mixture. Thus, to improve the adhesion of the coating, the micronized INHIBICOR®1000 particles were neutralized by exposing the micronized particles to a base. In an example, the micronized particles were placed in water and the neutralizing was performed by titrating to neutral pH (e.g., pH of 7) with 1M NaOH. A coating prepared from the micronized and neutralized corrosion inhibiting particles was prepared under similar conditions as those coatings described for FIGS. 7A and 7B, and the results of forming a coating on a test substrate, the coating comprising micronized particles that have been neutralized by exposing them to a base, is shown in FIG. 7C. A comparison of FIGS. 7B and 7C shows that the "river like" patterns are no longer present as a result of the neutralizing step, showing that neutralization improved the adhesion of to the Al 2024 panel.

Figure 8:
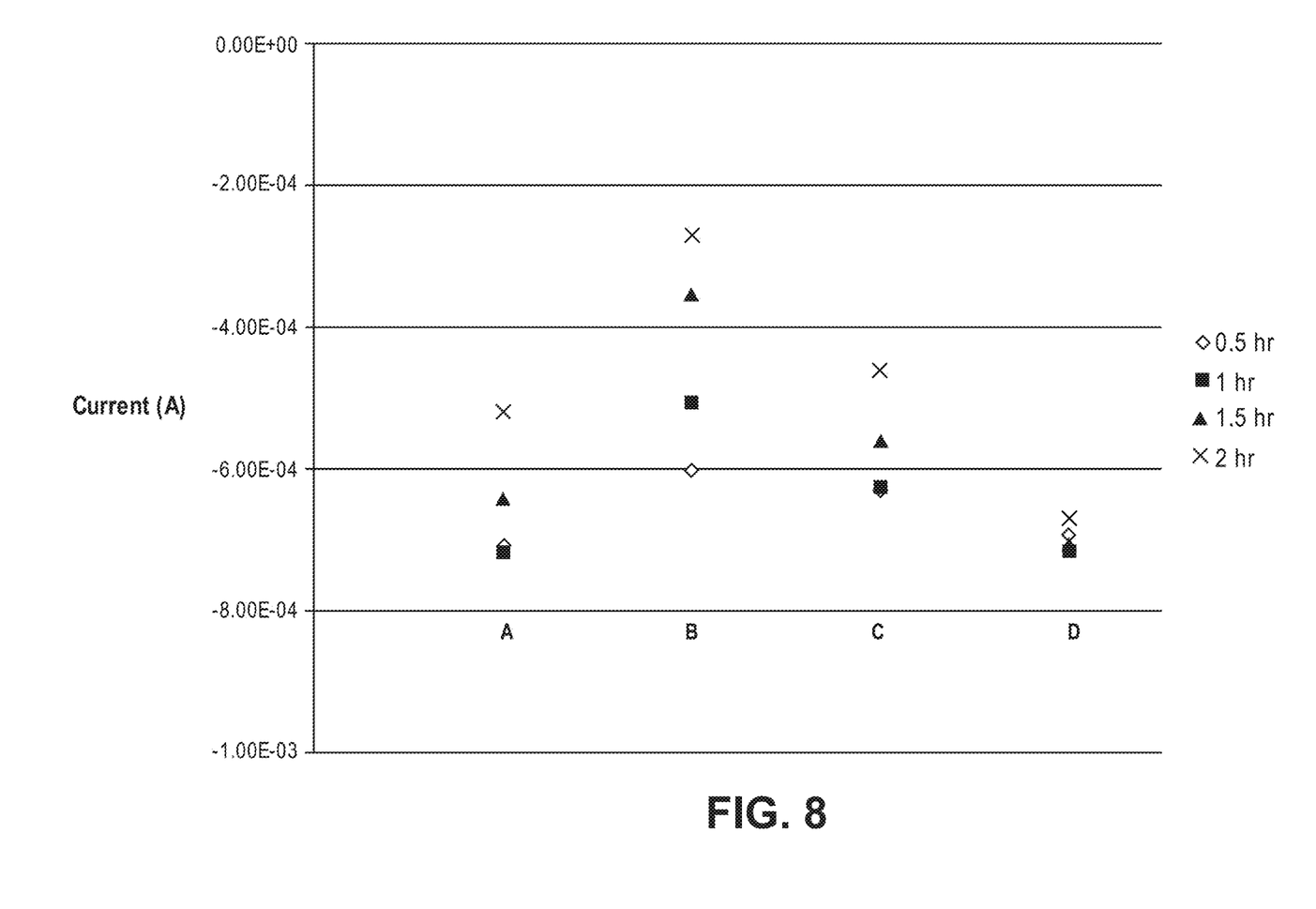
FIG. 8 is a Linear Sweep Voltammetry (LSV) graph showing effects of micronizing and neutralizing INHIBICOR® 1000 particles.
Figure 9:
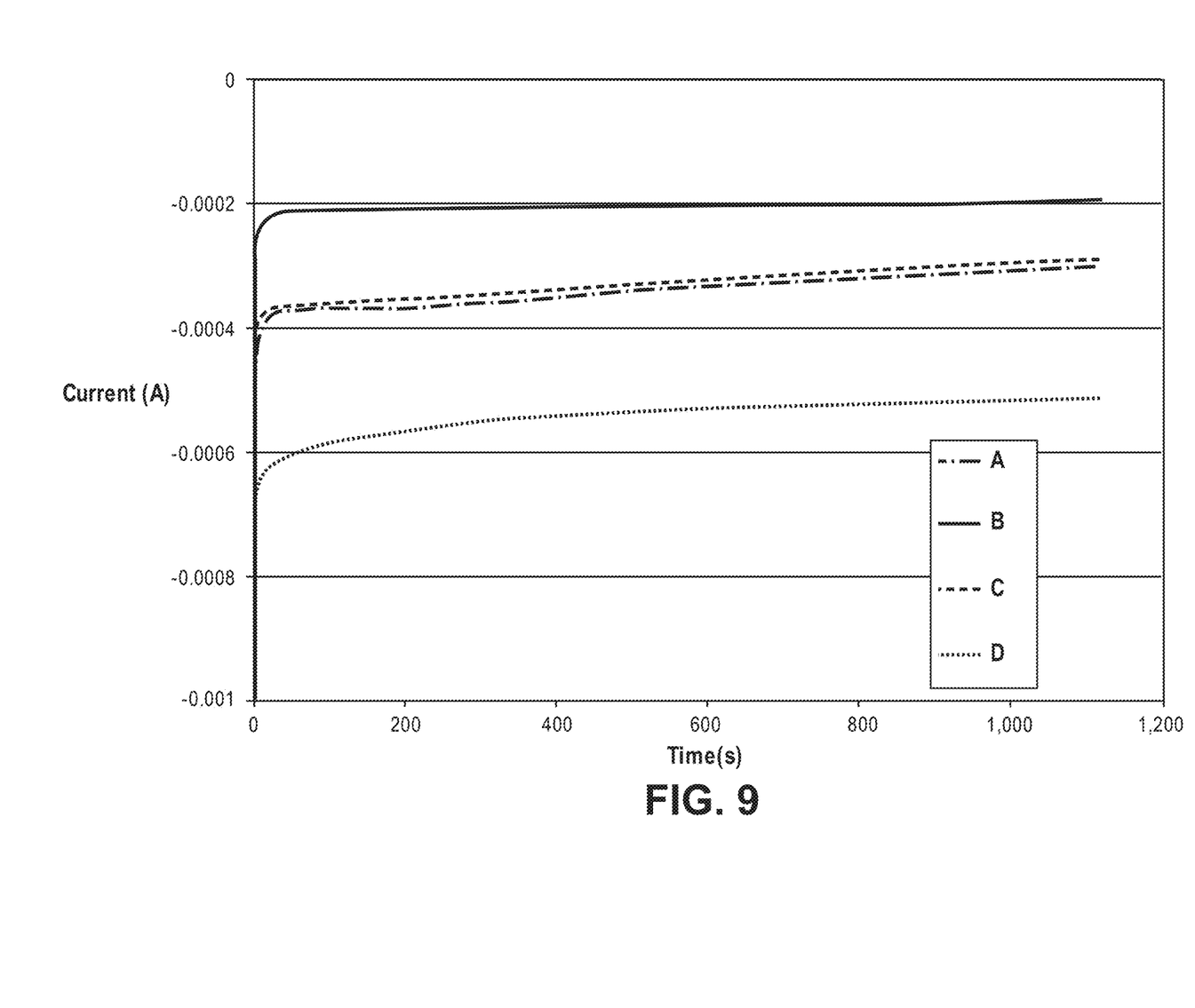
FIG. 9 is a chronoamperometry plot showing effects of micronizing and neutralizing INHIBICOR® 1000 particles.

The results of Linear Sweep Voltammetry (LSV) (FIG. 8) and Chronoamperometry (FIG. 9) show effects of micronizing and neutralizing INHIBICOR 1000® particles as tested for the coatings as described above for FIGS. 7A-7C. As shown in FIG. 8, micronized corrosion inhibiting particles as described herein (B) also improved the inhibition of oxygen-reduction-reaction (ORR) at the surface of a Cu rotating disk relative to coatings that included as-is, unmicronized INHIBICOR 1000® particles (A). As shown by the results in FIG. 3 results, a larger amount of the inhibitor leached out of the coating as was visible by the decreasing ORR current with time. Meanwhile, neutralizing the micronized particles (C) slightly decreased the coating's ability to inhibit ORR. When the panel was coated heavily (D) with the same solution (C) (2 min spray time as compared to ~30 sec) leaching of the inhibitor out of the coating was negligible in a 2 hr time-frame.

While the present teachings have been illustrated with respect to one or more implementations, alterations and/or modifications may be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or descriptions of the present teachings. It will be appreciated that structural components and/or processing stages may be added or existing structural components and/or processing stages may be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "about" indicates that the value listed may be somewhat altered, as long as the alteration does not result in nonconformance of the process or structure to the illustrated descriptions. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

Other implementations will be apparent to those skilled in the art from consideration of the specification and practice of what is described herein. It is intended that the specification and examples be considered as exemplary only, with a true scope and spirit of the implementations being indicated by the following claims.

What is claimed is:

1. A method for preparing a non-chrome corrosion inhibitor coating composition, the method comprising:
   providing a thiol-containing, chemically reactive corrosion-inhibitor;
   micronizing the corrosion inhibitor to form micronized particle cores having a particle size in a range of about 100 nm to about 5 µm; and
   forming a protectant on a surface of the micronized particle cores by covalently bonding at least one of a reactive component of a protectant-forming composition to a thiol group of the micronized particle cores, the protectant forming composition comprising a material chosen from epoxy and poly(meth)acrylates, the protectant being configured as shells surrounding the micronized particle cores, the micronized particle cores and protectant together forming non-chrome corrosion-inhibiting particles; and
   incorporating the non-chrome corrosion-inhibiting particles into a coating composition.

2. The method of claim 1, wherein the corrosion inhibitor is water soluble.

3. The method of claim 1, wherein the corrosion inhibitor comprises a polydisulfide.

4. The method of claim 1, wherein the corrosion-inhibitor comprises a mercaptan-terminated poly sulfide.

5. The method of claim 1, wherein the corrosion inhibitor comprises a mercaptan-terminated polysulfide of dimercaptothiadiazole.

6. The method of claim 1, further comprising chemically neutralizing the surface of the micronized particle cores during or after micronizing.

7. The method of claim 6, wherein chemically neutralizing the surface comprises exposing the micronized particle cores to a base.

8. The method of claim 7, wherein the base is selected from NaOH or KOH.

9. The method of claim 7, wherein the protectant-forming composition comprises the epoxy.

10. The method of claim 1, wherein the protectant is water-permeable, and wherein dissolved corrosion-inhibitor can diffuse through the protectant.

11. The method of claim 1, wherein the coating composition comprises a carrier comprising at least one selected from the group consisting of an epoxy resin and an olefin resin, and the protectant reduces cross-linking between the core and the epoxy resin or the olefin resin.

12. The method of claim 1, wherein the coating composition is a paint.

13. The method of claim 1, wherein the protectant-forming composition comprises the poly(meth)acrylates.

14. A method for preparing a non-chrome corrosion inhibitor coating composition, the method comprising:
   providing a thiol-containing, chemically reactive corrosion-inhibitor;
   micronizing the corrosion inhibitor to form micronized particle cores having a particle size in a range of about 100 nm to about 5 µm to form a micronized core;
   forming a protectant on a surface of the micronized particle cores by covalently bonding at least one of a reactive component of a protectant-forming composition to a thiol group of the micronized particle cores, the protectant forming composition comprising an epoxy, the protectant being configured as shells surrounding the micronized particle cores, the micronized particle cores and protectant together forming non-chrome corrosion-inhibiting particles; and
   incorporating the non-chrome corrosion-inhibiting particles into a coating composition.

15. The method of claim 14, wherein the corrosion inhibitor is water soluble.

16. The method of claim 14, wherein the corrosion inhibitor comprises a polydisulfide.

17. The method of claim 14, wherein the corrosion-inhibitor comprises a mercaptan-terminated polysulfide.

18. The method of claim 14, wherein the corrosion inhibitor comprises a mercaptan-terminated polysulfide of dimercaptothiadiazole.

19. The method of claim 14, further comprising chemically neutralizing the surface of the particle cores during or after micronizing.

20. The method of claim 14, wherein the coating composition is a paint.

* * * * *